United States Patent
Allon et al.

(10) Patent No.: US 9,655,848 B2
(45) Date of Patent: May 23, 2017

(54) LIPOSOMES FOR IN-VIVO DELIVERY

(71) Applicant: Technion Research and Development Foundation Limited, Haifa (IL)

(72) Inventors: Nahum Allon, Maccabim (IL); Moshe Gavish, Tel Aviv (IL)

(73) Assignee: Technion Research & Development Foundation Limited, Haifa (IL)

(*) Notice: Subject to any disclaimer, the term of this patent is extended or adjusted under 35 U.S.C. 154(b) by 0 days.

(21) Appl. No.: 14/440,834

(22) PCT Filed: Nov. 19, 2013

(86) PCT No.: PCT/IL2013/050957
§ 371 (c)(1),
(2) Date: May 5, 2015

(87) PCT Pub. No.: WO2014/076709
PCT Pub. Date: May 22, 2014

(65) Prior Publication Data
US 2015/0283078 A1 Oct. 8, 2015

Related U.S. Application Data

(60) Provisional application No. 61/727,809, filed on Nov. 19, 2012, provisional application No. 61/727,792, filed on Nov. 19, 2012.

(51) Int. Cl.
A61K 9/127 (2006.01)
A61K 47/42 (2006.01)
A61K 31/365 (2006.01)
C07K 1/107 (2006.01)
C07K 7/00 (2006.01)
C12N 15/88 (2006.01)

(52) U.S. Cl.
CPC .......... *A61K 9/1272* (2013.01); *A61K 9/1277* (2013.01); *A61K 31/365* (2013.01); *A61K 47/42* (2013.01); *C07K 1/1077* (2013.01); *C07K 7/00* (2013.01); *C12N 15/88* (2013.01); *C12N 2320/32* (2013.01); *C12N 2320/53* (2013.01); *C12N 2500/36* (2013.01); *C12Q 2563/161* (2013.01)

(58) Field of Classification Search
None
See application file for complete search history.

(56) References Cited

U.S. PATENT DOCUMENTS

| 2002/0012998 A1* | 1/2002 | Gonda ................. A61K 9/1271 435/458 |
| 2003/0166529 A1 | 9/2003 | Mileusnic et al. |
| 2009/0221513 A1* | 9/2009 | Rose ...................... A61K 38/06 514/1.1 |
| 2010/0099609 A1 | 4/2010 | John et al. |

FOREIGN PATENT DOCUMENTS

| CN | 101351214 A | 1/2009 | |
| GB | 2002083729 A2 * | 10/2002 | ............. C07K 14/47 |
| JP | WO9409808 * | 5/1994 | ............. A61K 37/02 |
| WO | 2009150686 A1 | 12/2009 | |

OTHER PUBLICATIONS

Re et al. Functionalization of liposomes with ApoE-derived peptides at different density affects cellular uptake and drug transport across a blood-brain barrier model. Nanomedicine. Oct. 2011;7(5):551-9. doi: 10.1016/j.nano.2011.05.004. Epub May 20, 2011.*

Thomas M Barchet & Mansoor M Amiji. Challenges and opportunities in CNS delivery of therapeutics for neurodegenerative diseases, Expert Opinion on Drug Delivery. 2009; 6(3): 211-225.*

Re, Francesca et al: Functionalization with ApoE-derived peptides enhances the interaction with brain capillary endothelial cells of nanoliposomes binding amyloid-beta peptide. Journal of Biotechnology 156, Jul. 6, 2011; pp. 341-346.

Re, Francesca et al: Functionalization of liposomes with ApoE-derived peptides at different density affects cellular uptake and drug transport across a blood-brain barrier model. Nanomedicine: Nanotechnology, Biology and Medicine; Oct. 2011, pp. 551-559; vol. 7, Issue 5.

Nahum, Allon: A new liposome-based gene delivery system targeting lung epithelial cells using endothelin antagonist; Journal of Controlled Release 160 (2012); pp. 217-224.

Michelia, Maria-Rita: Lipid-Based Nanocarriers for CNS-Targeted Drug Delivery; Recent Patents on CNS Drug Discovery Apr. 7, 2012; pp. 71-86.

Print-out of http://www.nextprot.org/db/entry/NX_P02649/sequence—2 pages, printed on Mar. 23, 2016.

* cited by examiner

*Primary Examiner* — Satyanarayana R Gudibande
*Assistant Examiner* — Jia-Hai Lee
(74) *Attorney, Agent, or Firm* — Roach Brown McCarthy Gruber P.C.; Kevin D. McCarthy

(57) ABSTRACT

The present invention provides a liposome based composition wherein the liposome includes a peptide conjugated thereto via a peptide bond, wherein the peptide includes a spacer amino acid and a short Apolipoprotein E recognition sequence or a short Amyloid beta recognition sequence. This invention further provides a process for making the liposome and methods of utilizing the liposome based composition for therapeutic and diagnostic purposes.

27 Claims, 3 Drawing Sheets

(APP328-332)
A-H-R-E-R-
M-S-COOH (hApoE [141-150])
A-L-R-K-L-R-K-R-
L-L-R-COOH

A

B

LIPOSOMES FOR IN-VIVO DELIVERY

FIELD OF THE INVENTION

The present invention provides, inter-alia, a liposome based composition wherein a short Apolipoprotein E recognition peptide and/or a short Amyloid beta recognition peptide is/are conjugated to the liposome.

BACKGROUND OF THE INVENTION

Neurodegenerative diseases, cancer and infections of the brain become more prevalent as populations become older. However, despite the relatively high blood flow in the brain, the brain is probably one of the least accessible organs for the delivery of active pharmacological compounds. There are two physiological barriers separating the brain from free supply via the blood system. The first barrier is the blood-brain barrier (BBB) and the second barrier is the blood-cerebrospinal fluid barrier (BCSFB).

Since the surface area of the human BBB is estimated to be 5000 times greater than that of the BCSFB, the BBB is considered to be the main barrier controlling the uptake of molecules such as drugs into the brain parenchyma and the target for delivering drugs to the brain. The BBB is defined by the microvasculature of the brain, which consists of a monolayer of polarized endothelial cells connected by complex tight junctions. The function of the BBB is dynamically regulated by various cells, including astrocytes, neurons and pericytes.

The endothelial cells are separated from these other cells by a basal lamina, whose components such as type IV collagen, laminin, fibronectin and heparan sulfate may be involved in drug transport, as some of them are negatively charged.

The BBB is characterized by complex tight junctions between the endothelial cells of the brain capillaries known for their low endocytic activity. However, the BBB also contains a number of specific transport and enzyme systems that regulate molecular traffic across the blood capillaries. The barrier and its selective transport system also play an important role in the homeostatic regulation of the brain microenvironment necessary for stable and coordinated activity of neurons. Circulating molecules can cross the BBB via the: (i) lipid mediated transport of small molecules by free diffusion and (ii) catalyzed transport. The latter includes carrier-mediated transport (CMT) for low molecular weight nutrient or receptor-mediated transport (RMT) for circulating peptides and plasma proteins. The BBB is therefore the major obstacle to drugs that may combat diseases affecting the central nervous system (CNS), from getting within the proximity of affected neurons.

Several strategies for delivering drugs to the CNS have been developed, in order to enhance the capacity of therapeutic molecules to cross the BBB: (i) an injectable composition comprising compounds that permeate the BBB; (ii) the drug of choice is covalently coupled to a vector for receptor-mediated or adsorption-mediated trans-cytosis; and (iii) the drug itself is modified in such a way that enables its permeation through the BBB.

These strategies have undesired side effects such as the non-selective overall enhanced permeability of the BBB i.e. impairment of the BBB function; interference with the therapeutic capacity of the drug itself. Furthermore, modifications of drugs do not necessarily contribute to the specificity of the treatment and may even reduce it by directing the compounds to tissues and organs that are not the "natural" target of the drug.

SUMMARY OF THE INVENTION

In one embodiment, the present invention provides a composition comprising a liposome and a peptide conjugated to the liposome via a peptide bond, wherein the peptide comprises at least one spacer amino acid followed by the amino acid sequence of any one or more of SEQ ID NOs: 1-6.

In a further embodiment, the invention provides that the liposome is composed of: cholesterol (Ch), 1,2-dioleoyl-sn-glycero-3-phosphocholine (DOPC), 1,2-dioleoyl-sn-glycero-3-phosphoethanolamine (DOPE).

In a further embodiment, the invention provides that the liposome is composed of: cholesterol (Ch), 1,2-dioleoyl-sn-glycero-3-[phosphor-L-serine] (DOPS), 1,2-dioleoyl-sn-glycero-3-phosphoethanolamine (DOPE). In a further embodiment, the invention provides that the weight ratio of: Ch, DOPC, and DOPE is about 1:1:1. In a further embodiment, the invention provides that the weight ratio of: Ch, DOPS, and DOPE is about 1:1:1.

In a further embodiment, the invention provides a method for treating a subject afflicted with a brain pathology comprising administering to the subject the composition comprising a liposome and a peptide conjugated to the liposome via a peptide bond, wherein the peptide comprises at least one spacer amino acid followed by the amino acid sequence of any one or more of SEQ ID NOs: 1-6, thereby treating a subject afflicted with a brain pathology.

In a further embodiment, the invention provides a process for the preparation of a liposome conjugated to a peptide comprising at least one spacer amino acid followed by the amino acid sequence of any one or more of SEQ ID NOs: 1-6, comprising the steps: (a) Dissolving in chloroform: (1) Cholesterol (Ch), 1,2-dioleoyl-sn-glycero-3-phosphocholine (DOPC), and 1,2-dioleoyl-sn-glycero-3-phosphoethanolamine (DOPE); or (2) Cholesterol (Ch), 1,2-dioleoyl-sn-glycero-3-[phosphor-L-serine] (DOPS), and 1,2-dioleoyl-sn-glycero-3-phosphoethanolamine (DOPE); (b) Adding to the mixture of step (a) a peptide comprising at least one spacer amino acid followed by the amino acid sequence of any one or more of SEQ ID NOs: 1-6 conjugated to 1,2-dioleoyl-sn-glycero-3-succinate at a concentration of 0.1-1 mol %; (c) Removing the chloroform and obtaining a dried lipid film; and (d) Hydrating the dried lipid film in an isotonic buffer; and optionally (e) loading a hydrophilic drug onto the liposome in an isotonic buffer in an amount equal to w/w ratio in the range from 2:1 to 100:1 drug to dry liposome; and/or (f) loading a lipid soluble drug onto the liposome comprising: (1) Heating a loading composition comprising the lipid soluble drug and the liposome to a temperature that is 0.01° C. to 5° C. above the phase-inversion temperature thus obtaining a water in oil emulsion; and (2) Cooling the loading composition to a temperature that is 0.01° C. to 10° C. below the phase-inversion temperature thus obtaining an oil in water emulsion, thereby obtaining a liposome conjugated to a peptide comprising at least one spacer amino acid followed by the amino acid sequence of any one or more of SEQ ID NOs: 1-6.

In a further embodiment, the invention provides a liposome obtained by the process described herein.

DETAILED DESCRIPTION OF THE INVENTION

Figure 1:
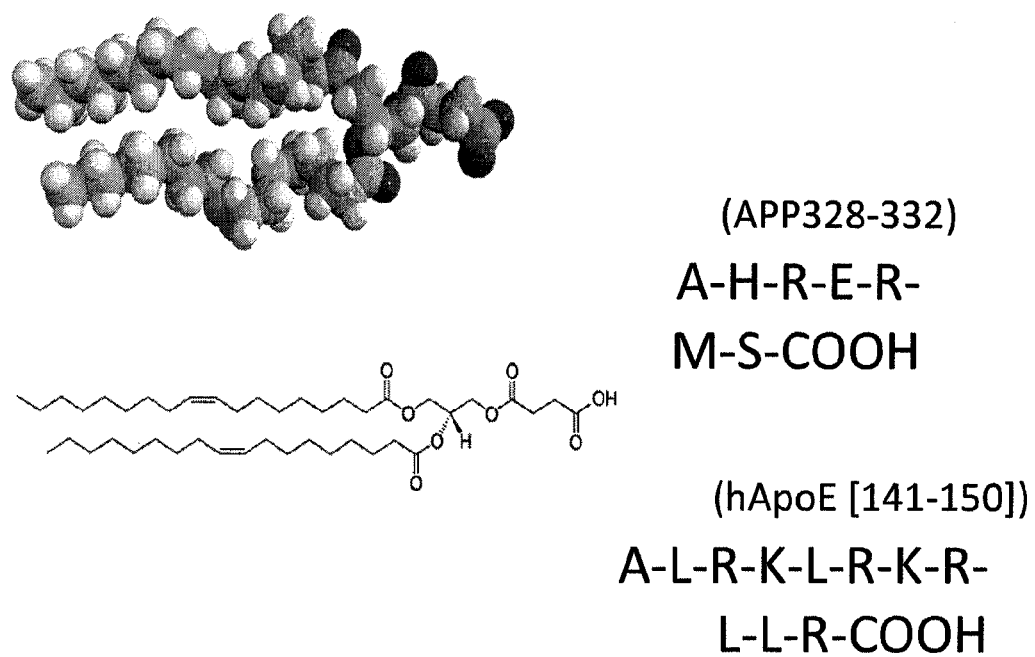
FIG. 1. Is a scheme showing the sequence for the first target peptide and the second target peptide and the dioleoyl succinate to which the spacer amino acid is bound to via a peptide bond, thus conjugating the peptide to the liposome.

The present invention provides, in one embodiment, a drug-delivery system that ensures the crossing of the drug over the BBB in a safe, controlled, and effective manner without disrupting the integrity and/or the selectivity of the BBB. In another embodiment, provided herein, a substance such as a marker (indicator, a contrast agent)-delivery system that ensures the crossing of the substance over the BBB in a safe, controlled, and effective manner without disrupting the integrity and/or the selectivity of the BBB.

The present invention further provides a strategy that enhances drug and/or substance delivery across the BBB by utilizing liposome-based carriers. The liposomes, in some embodiments, transfer any desired modified or unmodified molecules (such as therapeutic molecules, labeling molecules or markers) through the BBB without the undesired disposition effect of drugs/substances into other, non-target, organs or tissues and without tampering with the integrity of the endothelial tissue which supports and protects the brain from molecules carried by the vascular system.

In another embodiment, the present invention provides a liposome comprising an anchored BBB recognition peptide or peptides such as any one or more of the peptides provided in SEQ ID NOs: 1-6 for transferring any desired molecule (such as therapeutic molecules, labeling molecules or markers) through the BBB without the undesired disposition effect of drugs/substances into other non-target organs or tissues and without tampering with the integrity of the endothelial tissue which supports and protects the brain from molecules carried by the vascular system. In another embodiment, the present invention provides a method based on a liposomal carrier for delivering compounds (such as therapeutic compounds) of any kind through the BBB in a controlled and a reproducible manner.

In another embodiment, the present invention provides that the anchored BBB recognition peptide targets a BBB transporter such as Amyloid-beta (Aβ) and/or Apolipoprotein E (ApoE). In another embodiment, the present invention provides that the anchored BBB recognition peptide is accumulated and affects by a specific mechanism in the brain. In another embodiment, the present invention provides that the anchored BBB recognition peptide facilitates the penetration of the liposomal carrier to the brain from a circulatory system (blood) by binding to a specific transporter located within the BBB. In another embodiment, the present invention provides that the anchored BBB recognition peptide has minimal or no other functional effects.

In another embodiment, the exceptional efficacy of the present composition comprising a liposome and an anchored BBB recognition peptide is unexpected in view of the state of the art. In another embodiment, the present composition comprising a liposome and an anchored BBB recognition peptide has very law immunogenicity. In another embodiment, the present composition comprising a liposome and an anchored BBB recognition peptide overcomes the hurdles associated with immunogenicity of other protein that were attached by different means to the liposome. In another embodiment, the present composition comprising a liposome and an anchored BBB recognition peptide is characterized by high efficiency of uptake of the substance (drug or marker). The ratio of liposome to therapeutic molecule was also optimized for target cell type. This optimization of the liposome-therapeutic molecule complex, in combination with the addition of a targeting ligand, yields substantially improved efficacy when administered in conjunction with radiation or chemotherapies. In another embodiment, the liposome carrier of the present invention increases the therapeutic window of the drug it carries. Those skilled in the art will be able to optimize the complexes for delivering a variety of therapeutic molecules to a variety of cell types.

In another embodiment, the present invention provides that a liposome comprising an anchored BBB recognition peptide connects to a recognition site in the BBB and penetrates or mediates the penetration to the brain. In another embodiment, the present invention provides that a liposome comprising an anchored BBB recognition peptide connects to a recognition site in the BBB thereby allowing the release of the substances/drugs of choice present in the liposome or on the liposome into a pre-determined site in the brain.

In another embodiment, the term "comprising" includes the term "consisting". In another embodiment, the term "comprising" is substituted by the term "consisting".

The Composition

In another embodiment, the present invention provides a composition comprising a liposome and a peptide conjugated to the liposome, wherein the peptide comprises at least one spacer amino acid followed by the amino acid sequence RERMS (SEQ ID NO: 1). In another embodiment, the present invention provides a composition comprising a liposome and a peptide conjugated to the liposome, wherein the peptide comprises at least one spacer amino acid followed by the amino acid sequence LRKLRKRLLR (SEQ ID NO: 2). In another embodiment, the present invention provides a composition comprising a liposome and a peptide conjugated to the liposome, wherein the peptide comprises the amino acid sequence ALRKLRKRLLR (SEQ ID NO: 3). In another embodiment, the present invention provides a composition comprising a liposome and a peptide conjugated to the liposome, wherein the peptide comprises the amino acid sequence ARERMS (SEQ ID NO: 4). In another embodiment, the present invention provides a composition comprising a liposome and a peptide conjugated to the liposome, wherein the peptide comprises the amino acid sequence HRERMS (SEQ ID NO: 5). In another embodiment, the present invention provides a composition comprising a liposome and a peptide conjugated to the liposome, wherein the peptide comprises the amino acid sequence AHRERMS (SEQ ID NO: 6). In another embodiment, the invention provides a peptide connected via a peptide bond to at least one spacer amino acid. In another embodiment, at least one spacer amino acid is Alanine. In another embodiment, the present invention provides a composition comprising a liposome and at least one of the peptides described herein. In another embodiment, the present invention provides a composition comprising a liposome and any combination of the peptides described herein.

In another embodiment, the peptide is a targeting ligand. In another embodiment, conjugated is conjugated via a peptide bond between a carboxyl end of a succinate group within the liposomal lipid bilayer and the amino group of at least one spacer amino acid. In another embodiment, succinate group includes succinic acid or salts formed by neutralizing succinic acid. In another embodiment, a spacer amino acid is any amino acid. In another embodiment, a spacer amino is an amino acid added to the peptide of the invention for conjugation purposes.

In another embodiment, the present invention provides a composition comprising a liposome, a peptide conjugated to the liposome, and a drug. In another embodiment, the drug is a brain therapeutic compound. In another embodiment, the present invention provides a composition comprising a liposome, a peptide conjugated to the liposome, and a marker. In another embodiment, the marker is a probe. In another embodiment, the marker is a brain probing agent.

In another embodiment, a brain therapeutic compound is a compound that has an established therapeutic effect within the brain. In another embodiment, a brain therapeutic compound is a compound capable of treating brain pathology. In another embodiment, the brain pathology is selected from the group comprising: acoustic neuroma, acquired brain injury, agenesis corpus callosum, Alzheimer's disease, amyotrophic lateral diseases, aneurysm, aphasia, arteriovenous malformation, batten disease, behcet's disease, blepharospasm, brain tumour, brain cancer, cerebral lupus, cerebral palsy, cervical dystonia, charcot-marie-tooth disorder, chiari malformation, chronic inflammatory demyelinated polyneuropathy, coma and persistent vegetative state, concussion, creutzfedlt-jakob disease, dementia (non-alzheimer type), down syndrome, dysautonomia, dyslexia, dyspraxia, dystonia, encephalitis, epilepsy, essential tremor, friedreich's ataxia, gaucher disease, guillain-barre syndrome, huntington's disease, hydrocephalus, intracranial hypertension, leukodystrophy, meniere's disease, meningitis, meningococcal disease, migraine, motor neurone disease, multiple sclerosis, muscular dystrophy, myasthenia gravis, narcolepsy, Parkinson's disease, peripheral neuropathy, Prader-Willi syndrome, progressive supranuclear palsy, restless legs syndrome, Rett syndrome, Shy Drager syndrome, sleep disorders, spasmodic dysphonia, stroke, subarachnoid haemorrhage, sydenham's chorea, Tay-Sachs disease, Tourette syndrome, transient ischaemic attack, transverse myelitis, trigeminal neuroalgia, tuberous sclerosis, or von-Hippel-Lindau syndrome.

In another embodiment, a brain probing agent is an agent that binds a site within the brain and is detectable by radiology. In another embodiment, a brain-probing agent is an agent that recognizes a cell or a protein within the brain. In another embodiment, a brain probing agent is an agent that recognizes a defective cell or a defective protein within the brain. In another embodiment, a brain probing agent is an agent that specifically binds and/or recognizes an epitope within the brain. In another embodiment, a brain-probing agent is an agent that binds and/or recognizes an epitope associated with brain pathology. In another embodiment, a brain-probing agent is used for the diagnosis of brain pathology. In another embodiment, a brain-probing agent probes brain activity.

In another embodiment, the composition is a freeze-dried composition. In another embodiment, the composition is in the form of a powder. In another embodiment, the composition further comprises a substance anchored to the liposomal membrane or engulfed within the liposome. In another embodiment, a liposome such as described herein comprises a drug or a substance encapsulated within it such as but not limited to: a gene or a fragment thereof, siRNA, a plasmid containing a gene therapy or a gene producing drug or a specific toxin against a disease (cancer), an antisense DNA, etc. In another embodiment, the composition is a freeze-dried, empty liposome composition. In another embodiment, the composition further comprises a phospholipid. In another embodiment, the composition further comprises an electrolyte. In another embodiment, the composition further comprises a drug. In another embodiment, the composition further comprises a solution. In another embodiment, the composition further comprises an aqueous solution. In another embodiment, the composition further comprises an isotonic solution. In another embodiment, a liposome such as described herein is a chelating polymer-bearing liposome.

The Liposome's Lipids

In another embodiment, a liposome suitable for use in the composition of the present invention includes those composed primarily of vesicle-forming lipids. In another embodiment, a vesicle-forming lipid is a lipid that (a) can form spontaneously into bilayer vesicles in water, as exemplified by the phospholipids (PLs), or (b) is stably incorporated into lipid bilayers, with its hydrophobic moiety in contact with the interior, hydrophobic region of the bilayer membrane, and its head group moiety oriented toward the exterior, polar surface of the membrane. In another embodiment, the phospholipids are alkylating PLs that can be part of the liposomes while acting as anticancer agents. In another embodiment, a phospholipid is HePC. In another embodiment, the phospholipid is ErPC3. In another embodiment, the phospholipid is a mixture of HePC, ErPC3, or any other PL.

In another embodiment, the vesicle-forming lipids are ones having two hydrocarbon chains, acyl chains, and a head group, either polar or nonpolar. In another embodiment, synthetic vesicle-forming lipids and naturally-occurring vesicle-forming lipids are utilized, including the phospholipids, such as phosphatidylcholine, phosphatidylethanolamine, phosphatidic acid, phosphatidylinositol, and sphingomyelin, where the two hydrocarbon chains are typically between about 14-22 carbon atoms in length, and have varying degrees of unsaturation.

In another embodiment, a liposome such as described herein is composed of natural phospholipids. In another embodiment, a liposome such as described herein is composed of mixed lipid chains with surfactant properties. In another embodiment, a liposome such as described herein is composed of phosphatidylethanolamine. In another embodiment, a liposome such as described herein is a multilamellar vesicle (MLV). In another embodiment, a liposome such as described herein is a small unilamellar vesicle (SUV). In another embodiment, a liposome such as described herein is a large unilamellar vesicle (LUV). In another embodiment, a liposome such as described herein is a cochleate vesicle.

In another embodiment, a liposome composition of the invention comprises any compositions described in: U.S. Pat. Nos. 4,983,397; 6,476,068; 5,834,012; 5,756,069; 6,387,397; 5,534,241; 4,789,633; 4,925,661; 6,153,596; 6,057,299; 5,648,478; 6,723,338; 6,627,218; U.S. Pat. App. Publication Nos: 2003/0224037; 2004/0022842; 2001/0033860; 2003/0072794; 2003/0082228; 2003/0212031; 2003/0203865; 2004/0142025; 2004/0071768; International Patent Applications WO 00/74646; WO 96/13250; WO 98/33481; Papahadjopolulos D, Allen T M, Gabizon A, et al. "Sterically stabilized liposomes. Improvements in pharmacokinetics and antitumor therapeutic efficacy" Proc Natl Acad Sci U.S.A. (1991) 88: 11460-11464; Allen T M, Martin F J. "Advantages of liposomal delivery systems for anthracyclines" Semin Oncol (2004) 31: 5-15 (suppl 13). Weissig et al. Pharm. Res. (1998) 15: 1552-1556, all of which are hereby incorporated by reference in their entireties.

In another embodiment, a liposome composition of the invention comprises a lipid mixture. In another embodiment, a liposome composition of the invention comprises a substance to be delivered to the brain. In another embodiment, the substance is a drug or labeled compound. In another embodiment, a liposome composition of the invention confers the benefit of reducing side effects from the drug or labeled compound and/or prevents degradation and/or loss of efficacy of the drug or labeled compound.

In another embodiment, a liposome composition of the invention comprises an N-(omega)-dicarboxylic acid-derivatized phosphatidyl ethanolamine, an encapsulated drug or labeled compound. In another embodiment, one or more phospholipids is POPC, DPPC, DMPC, or DSPC, and at least one additional lipid such as cholesterol.

In another embodiment, the phospholipid is a phosphatidylcholine, phosphatidic acid, phosphatidylserine or phosphatidylglycerol. In another embodiment, the phospholipid is a neutral phospholipid. In another embodiment, the phospholipid is a phosphatidylcholine. In another embodiment, phosphatidyl choline includes a moiety of a saturated fatty acid. In another embodiment, cholesterol includes a cholesterol derivative.

In another embodiment, a liposome composition of the invention comprises a cationic lipid. In another embodiment, a liposome composition of the invention comprises an anionic lipid. In another embodiment, a liposome composition of the invention is devoid of either an anionic lipid or a cationic lipid.

In some embodiments, the phospholipid is a phosphatidylcholine, including naturally occurring, semi-synthetic or synthetic phosphatidylcholines (e.g., DSPC, DMPC, etc.). In some embodiments, the phosphatidylcholine is a non-naturally occurring phosphatidylcholine. In some embodiments, the phosphatidylcholine is an acyl phosphatidylcholine (e.g., DMPC, DPPC, POPC, DSPC, etc.). Exemplary phospholipids include, but are not limited to: phosphatidylcholines (PCs), phosphatidic acid, phosphatidylserine, phosphatidylglycerol, etc. In some embodiments, the lipid-containing compositions do not include phosphatidylserine or phosphatidylglycerol.

In some embodiments, a liposome comprises a neutral lipid such as cholesterol or a cholesterol derivative (e.g., cholesterol pullulan, positively-charged cholesterol (e.g., DC-Chol)).

In some embodiments, the phospholipid is a phosphatidylcholine. In certain embodiments, the phosphatidylcholine may be, e.g., distearoyl phosphatidyl choline (DSPC), dimyristoyl phosphatidylcholine (DMPC), dipalmitoyl phosphatidylcholine (DPPC), palmitoyl oleoyl phosphatidylcholine (POPC), egg phosphatidylcholine (EPC), hydrogenated soya phosphatidylcholine (HSPC), etc. In particular embodiments, at least one phospholipid is a phosphatidylcholine. In certain of these embodiments, the phosphatidylcholine is DMPC. In other embodiments, the phosphatidylcholine is DSPC. In other embodiments, the phosphatidylcholine is DPPC. In other embodiments, the phosphatidylcholine is POPC. In other embodiments, the phosphatidylcholine is EPC. In other embodiments, the phosphatidylcholine is HSPC. In some embodiments, one phospholipid is included and is DMPC, DSPC, DPPC, POPC, EPC or HSPC. In particular embodiments where there are lipid-containing composition includes a single phospholipid (non-PE phospholipid), the phospholipid is DMPC. In other embodiments where the lipid-containing composition includes a single phospholipid (non-PE phospholipid), the phospholipid is DSPC. In other embodiments where the lipid-containing composition includes a single phospholipid (non-PE phospholipid), the phospholipid is DPPC. In other embodiments where the lipid-containing composition includes a single phospholipid (non-PE phospholipid), the phospholipid is POPC. In other embodiments where the lipid-containing composition includes a single phospholipid (non-PE phospholipid), the phospholipid is EPC. In other embodiments where the lipid-containing composition includes a single phospholipid (non-PE phospholipid), the phospholipid is HSPC.

In another embodiment, a liposome of the invention comprises cholesterol (Ch), 1,2-dioleoyl-sn-glycero-3-phosphocholine (DOPC), 1,2-dioleoyl-sn-glycero-3-phosphoethanolamine (DOPE). In another embodiment, a liposome of the invention comprises cholesterol (Ch), 1,2-dioleoyl-sn-glycero-3-[phosphor-L-serine] (DOPS), 1,2-dioleoyl-sn-glycero-3-phosphoethanolamine (DOPE). In another embodiment, the weight ratio of: Ch, DOPC, and DOPE is 0.2-2:0.2-2:0.2-2. In another embodiment, the weight ratio of: Ch, DOPS, and DOPE is 0.2-2:0.2-2:0.2-2. In another embodiment, the weight ratio of: Ch, DOPC, and DOPE is 1:1:1. In another embodiment, the weight ratio of: Ch, DOPS, and DOPE is 1:1:1. In another embodiment, the weight ratio is weight percent ratio.

In another embodiment, a liposome of the invention is prepared by a variety of techniques, such as those detailed in Szoka, F., Jr., et al., Ann. Rev. Biophys. Bioeng. 9:467 (1980), and specific examples of liposomes prepared in support of the present invention will be described below. In another embodiment, the liposomes are multilamellar vesicles (MLVs), which can be formed by simple lipid-film hydration techniques.

In another embodiment, pre-formed liposomes include a vesicle-forming lipid and a peptide conjugated thereto. In another embodiment, pre-formed liposomes include a vesicle-forming lipid and a peptide bound via a peptide bond to a succinate or to a succinic acid.

In another embodiment, the present invention further comprises the use of derivatized lipids. Methods of preparing derivatized lipids and of forming polymer-coated liposomes are described in U.S. Pat. Nos. 5,013,556, 5,631,018 and 5,395,619, which are incorporated herein by reference in their entirety. In another embodiment, the hydrophilic polymer is stably coupled to the lipid, or coupled through an unstable linkage which may allow coated liposomes to shed the coating of polymer chains as they circulate in the bloodstream or in response to a stimulus.

In another embodiment, therapeutic or diagnostic agents are incorporated into liposomes by standard methods, including (i) passive entrapment of a water-soluble compound by hydrating a lipid film with an aqueous solution of the agent, (ii) passive entrapment of a lipophilic compound by hydrating a lipid film containing the agent, and (iii) loading an ionizable drug against an inside/outside liposome pH gradient. Other methods, such as reverse evaporation phase liposome preparation, are also suitable.

In another embodiment, polynucleotides, oligonucleotides, other nucleic acids, such as a DNA plasmid, are entrapped in the liposome by condensing the nucleic acid in single-molecule form. In another embodiment, the nucleic acid is suspended in an aqueous medium containing protamine sulfate, spermine, spermidine, histone, lysine, mixtures thereof, or other suitable polycationic condensing agent, under conditions effective to condense the nucleic acid into small particles. In another embodiment, the solution of condensed nucleic acid molecules is used to rehydrate a dried lipid film to form liposomes with the condensed nucleic acid in entrapped form.

In another embodiment, a process for the preparation of a liposome conjugated to a peptide comprises the steps: (A) dissolving in an organic solvent such as chloroform: (1) Cholesterol (Ch), 1,2-dioleoyl-sn-glycero-3-phosphocholine (DOPC), and 1,2-dioleoyl-sn-glycero-3-phosphoethanolamine (DOPE); or (2) Cholesterol (Ch), 1,2-dioleoyl-sn-glycero-3-[phosphor-L-serine] (DOPS), and 1,2-dioleoyl-sn-glycero-3-phosphoethanolamine (DOPE); (B) adding to the mixture of step (A) a peptide of the invention and at least one spacer amino acid bound to the amino terminus of the peptide wherein the at least one spacer amino acid is conjugated to a succinate such as but not limited to: 1,2-dioleoyl-sn-glycero-3-succinate or 1,2-dioleoyl-sn-glycero-3-succinate; (C) remove the organic solvent thus obtaining a dried lipid film; and (D) hydrating the dried lipid film, thereby obtaining a liposome conjugated to a peptide.

In another embodiment, succinate is 1,2-dioleoyl-sn-glycero-3-succinate. In another embodiment, succinate is added at a concentration of 0.05-2 mol %. In another embodiment, succinate is added at a concentration of 0.1-1 mol %. In another embodiment, succinate is added at a concentration of 0.5-1 mol %. In another embodiment, succinate is added at a concentration of 0.05-0.5 mol %.

In another embodiment, hydrating is hydrating the dried lipid film in water. In another embodiment, hydrating is hydrating the dried lipid film in a buffer. In another embodiment, hydrating is hydrating the dried lipid film in an isotonic buffer. In another embodiment, hydrating is hydrating the dried lipid film in phosphate buffer saline.

In another embodiment, at least one spacer amino acid is an amino acid bridging between the succinate group within the liposome's bilayer and the peptide. In another embodiment, at least one spacer amino acid is one amino acid. In another embodiment, at least one spacer amino acid is two amino acids. In another embodiment, at least one spacer amino acid is three amino acids. In another embodiment, the recognition peptide comprises of any one of SEQ ID NOs: 1-6. In another embodiment, the recognition peptide consists any one of SEQ ID NOs: 1-6. In another embodiment, a liposome as described herein comprises more than one of the recognition peptides as described herein.

In another embodiment, the process for obtaining a liposome as described herein further comprises loading a hydrophilic drug onto or into a liposome. In another embodiment, the process for obtaining a liposome as described herein further comprises loading a hydrophilic drug onto or into a liposome in an aqueous solution. In another embodiment, the process for obtaining a liposome as described herein further comprises loading a hydrophilic drug onto or into a liposome in an isotonic buffer.

In another embodiment, loading of an agent into or onto the liposomes as describe herein is performed according to methods known to a person of skill in the art. In another embodiment, loading of a water soluble agent into or onto the liposomes includes dissolving the water soluble agent in an aqueous buffer and adding the liposomes to the solution comprising the water soluble agent, the solution is then dialyzed against the free buffer. In another embodiment, loading of a fat soluble agent may include a process of heating to a temperature above the phase-inversion temperature (PIT) of the fat insoluble agent followed by a cooling step.

In another embodiment, loading of a water soluble agent includes passive loading. In another embodiment, loading of a nucleic acid molecule includes passive loading. In another embodiment, loading of a water soluble agent includes remote loading as further exemplified hereinbelow.

In another embodiment, the drug's amount equals to w/w ratio in the range from 2:1 to 100:1 drug to dry liposome. In another embodiment, the drug's amount equals to w/w ratio in the range from 2:1 to 10:1 drug to dry liposome. In another embodiment, the drug's amount equals to w/w ratio in the range from 10:1 to 50:1 drug to dry liposome. In another embodiment, the drug's amount equals to w/w ratio in the range from 50:1 to 100:1 drug to dry liposome. In another embodiment, the drug's amount equals to w/w ratio in the range from 20:1 to 80:1 drug to dry liposome.

In another embodiment, the process for obtaining a liposome as described herein further comprises loading a lipid soluble drug onto or into a liposome. In another embodiment, the process for obtaining a liposome as described herein further comprises loading a lipid soluble drug onto or into a liposome by: (1) heating a loading composition comprising the lipid soluble drug and the liposome to a temperature that is 0.01° C. to 5° C. above the phase-inversion temperature thus obtaining a water in oil emulsion; (2) cooling the loading composition to a temperature that is 0.01° C. to 10° C. below the phase-inversion temperature thus obtaining an oil in water emulsion. In another embodiment, the above process for loading a lipid soluble drug onto or into a liposome includes at least one repetition of steps (1) and (2) thus forming at least one cycle. In another embodiment, a cycle is repeated at least twice. In another embodiment, a cycle is repeated 2-10 times. In another embodiment, a cycle is repeated 2-5 times.

In another embodiment, cooling is adding cold water. In another embodiment, cooling is refrigerating. In another embodiment, heating and cooling are performed at a rate of 0.5° C. to 20° C./min. In another embodiment, heating and cooling are performed at a rate of 1° C. to 10° C./min. In another embodiment, heating and cooling are performed at a rate of 1° C. to 5° C./min. In another embodiment, heating and cooling are performed at a rate of 2° C. to 8° C./min. In another embodiment, heating and cooling are performed at a rate of 5° C. to 10° C./min.

In another embodiment, heating is heating to a temperature of 60° C. to 100° C. In another embodiment, heating is heating to a temperature of 75° C. to 95° C. In another embodiment, heating is heating to a temperature of 75° C. to 85° C. In another embodiment, heating is heating to a temperature of 80° C. to 90° C. In another embodiment, heating is heating to a temperature of 90° C. to 100° C.

In another embodiment, cooling is cooling to a temperature of 40° C. to 80° C. In another embodiment, cooling is cooling to a temperature of 50° C. to 60° C. In another embodiment, cooling is cooling to a temperature of 60° C. to 70° C. In another embodiment, cooling is cooling to a temperature which is at least 5° C. below the maximal heating temperature. In another embodiment, cooling is cooling to a temperature which is at least 10° C. below the maximal heating temperature. In another embodiment, cooling is cooling to a temperature which is at least 15° C. below the maximal heating temperature. In another embodiment, cooling is cooling to a temperature which is at least 20° C. below the maximal heating temperature.

In another embodiment, the present invention provides a liposome or a composition comprising a liposome obtained by the process described herein.

Composition

In another embodiment, a liposome composition of the invention comprises a solution. In another embodiment, the lipid mixtures are free of solution. In another embodiment, the solution is an aqueous solution or a mixture of an aqueous solution and a water-miscible solvent. In another embodiment, a liposome composition of the invention further comprises a sugar such as sucrose. In another embodiment, a liposome composition of the invention further comprises one or more pharmaceutically acceptable carriers, excipients, diluents, stabilizers, or preservatives.

In another embodiment, the substance (drug and/or marker) is dissolved in a solution (e.g., an aqueous solution). In some embodiments, the solution includes a sugar (e.g., trehalose, maltose, sucrose, lactose, mannose, mannitol, glycerol, dextrose, fructose, etc.) The concentration of the sugar may be of several percent. For example sugar concentrations (v/v) of about 0.1-12; 0.5-12%, 1-12%, 2-8%, 2-6%, 2-5%, 2-4%, 2-5%, 2-6%, 2-8%, 2-9%, 2-10%, 4-10%, 4-9%, 4-8%, 4-6%, 3-4%, about 2%, about 3%, about 4%, about 5%, about 6%, about 7%, about 8%, about 9% or about 10%. In certain embodiments the solution includes a sugar and is aqueous. It is intended that the solution in which drug is dissolved can also contain additional components, including those known to the skilled artisan.

In certain embodiments, the sugar concentration is about 5%, about 7%, about 8%, about 9% or about 10%. In other embodiments, the sugar concentration is about 5% to about 10%. In some embodiments, the sugar is dextrose and the concentration of dextrose in the composition is about 5%. In some embodiments, the sugar is dextrose and the concentration of dextrose in the composition is 5-12%. In certain embodiments, the sugar is sucrose and the concentration of sucrose in the composition is 5-12%.

In some embodiments, the concentration of sugar in solution may be, for example about 50 mg/ml to about 150 mg/ml, about 50 mg/ml to about 130 mg/ml, about 50 mg/ml to about 120 mg/ml, about 50 mg/ml to about 100 mg/ml, about 80 mg/ml to about 100 mg/ml, about 90 mg/ml to about 150 mg/ml, about 90 mg/ml to about 130 mg/ml, about 60 mg/ml, about 80 mg/ml, about 90 mg/ml, about 100 mg/ml, about 110 mg/ml, about 105 mg/ml, about 120 mg/ml, or about 140 mg/ml.

The composition of the invention may also contain other ingredients known to those of skill in the art, such as, but not limited to, salts, buffers, sugar alcohol, etc. In another embodiment, the composition comprises sodium phosphate (e.g., monobasic and/or dibasic sodium phosphate).

In another embodiment, the concentration of sodium phosphate may be about 5 to about 15 mM. For example, from about 5 to about 12 mM, from about 5 to about 10 mM, from about 5 to about 7 mM, from about 7 to about 12 mM, from about 7 to about 15 mM, from about 9 to about 12 mM, about 5 mM, about 7 mM, about 10 mM, about 12 mM or about 15 mM.

In another embodiment, the sugar solution may additionally include about 1.0 to about 1.5 mg/ml sodium phosphate. For example, about 1.2 to about 1.5 mg/ml, 1.0 to about 1.7 mg/ml, 1.0 to about 2 mg/ml, 1.0 to about 2.5 mg/ml, 1.0 to about 3 mg/ml, 0.5 to about 3.5 mg/ml sodium phosphate.

In some embodiments, the composition/solution pH is about 6.5 to about 7.5, be about 6.7 to about 7.5, be about 7 to about 7.5, about 7, about 7.5, about 6.8, or about 6.5.

In another embodiment, a liposome such as described herein is a long-circulating liposome. In another embodiment, a liposome such as described herein further comprises a coating with inert, biocompatible polymers, such as PEG, which form a protective layer over the liposome surface and slow down liposome recognition by opsonins and therefore subsequent clearance.

In another embodiment, a liposome such as described herein comprises a removable PEG. In another embodiment, a liposome such as described herein comprises poly[N-(2-hydroxypropyl(methacrylamide)], poly-N-vinylpyrrolidones, L-amino-acid-based biodegradable polymer-lipid conjugate, polyvinyl alcohol, or any combination thereof.

Unlike the state of the art which utilizes: (1) PEG for attachment of a targeting ligand via a PEG spacer arm; or (2) attachment of a targeting ligand above a protecting group or polymer layer, by coupling it with the distal water-exposed terminus of activated liposome-grafted polymer molecule (Torchilin V P. Recent advances with liposomes as pharmaceutical carriers. Nat Rev Drug Discov. 2005 February; 4(2):145-60), the present invention makes use of a peptide bond via succinate.

In another embodiment, a liposome as described herein is a pH-sensitive liposome. In another embodiment, a liposome as described herein releases its content (the substance such as a drug) in pH-sensitive release manner. In another embodiment, a liposome as described herein is constructed from pH-sensitive components.

In another embodiment, a composition as described herein is a liposomal aerosol. In another embodiment, a composition as described herein is lyophilized.

Size and Zeta Potential

In another embodiment, the liposome's diameter is between 5 nm to 300 nm. In another embodiment, the liposome's diameter is between 10 nm to 200 nm. In another embodiment, the liposome's diameter is between 50 nm to 200 nm. In another embodiment, the liposome's diameter is between 50 nm to 150 nm. In another embodiment, the composition comprises liposomes having a mean diameter between 5 nm to 300 nm. In another embodiment, the composition comprises liposomes having a mean diameter between 50 nm to 200 nm. In another embodiment, the composition comprises liposomes having a mean diameter between 50 nm to 150 nm. In another embodiment, the composition comprises liposomes having a mean diameter between 50 nm to 250 nm. In another embodiment, the composition comprises liposomes having a mean diameter between 90 nm to 200 nm In another embodiment, the zeta potential of a liposome of the invention is from −10 mV to −200 mV. In another embodiment, the zeta potential of a liposome of the invention is from −50 mV to −150 mV. In another embodiment, the zeta potential of a liposome of the invention is from −50 mV to −130 mV. In another embodiment, the zeta potential of a liposome of the invention is from −60 to −120 mV. In another embodiment, the zeta potential of a liposome of the invention is from −50 to −100 mV. In another embodiment, the zeta potential of a liposome of the invention is from −75 mV to −90 mV. In another embodiment, the zeta potential of a liposome of the invention is from −80 mV to −90 mV. In another embodiment, the zeta potential of a liposome of the invention is from −80 mV to −85 mV. In another embodiment, the zeta potential of a liposome of the invention is from −85 mV to −90 mV. In another embodiment, the zeta potential of a liposome of the invention is from −75 mV to −85 mV. In another embodiment, the zeta potential of a liposome of the invention is from −70 mV to −90 mV. In another embodiment, the zeta potential of a liposome of the invention is −75 mV, −80 mV, −85 mV, −83 mV, −90 mV, −100 mV, −120 mV.

Drugs

In another embodiment, the substance to be carried by or via the circulatory system to the brain via the conjugated liposome of the invention is a drug. The drug is a substance or a compound having therapeutic activity in the brain. In another embodiment, the drug treats, ameliorates, or reduces the symptoms of a brain pathology such as listed above. In another embodiment, the drug is bound to the outer surface of the liposome. In another embodiment, the drug is encapsulated within the liposome.

In another embodiment, the drug is any antidepressant drug known to one of skill in the art. In another embodiment, the drug is any neurodegenerative ameliorating agent known to one of skill in the art. In another embodiment, the drug is any anti-brain cancer drug known to one of skill in the art. In another embodiment, the drug is any anti-psychotic drug known to one of skill in the art. In another embodiment, the drug is any agent having a ligand located within the brain. In another embodiment, the drug is any agent having a therapeutic effect within the brain.

In another embodiment, the drug is a compound or a gene. In another embodiment, the drug is an anticancer agent. In another embodiment, the amount of drug to be included in the liposome or composition as described herein can be readily determined by the skilled artisan in view of the teaching herein provided and depending on the drug selected and the use intended for the composition or formulation, taking into account factors specific to both the drug and the individual to be treated, as described further herein.

In another embodiment, the drug is a nucleic acid encoding for a sequence with anticancer properties. In another embodiment, the drug is complexed with the liposome. In another embodiment, the drug is encapsulated within the liposome. In another embodiment, the drug is a DNA molecule. In another embodiment, the drug is a RNA molecule. In another embodiment, the drug is a ribozyme. In another embodiment, the drug is a peptide nor a polypeptide. In another embodiment, the drug is a peptide nucleic acid. In another embodiment, the drug is a viral particle. In another embodiment, the drug is a chemical agent. In another embodiment, the drug is a cytokine. In another embodiment, the drug is a plasmid containing DNA and a suitable promoter for the de-novo generation of a drug or a toxin. In another embodiment, the drug is derived from a plasmid containing DNA and a suitable promoter for generation of a for the generation of a drug or a toxin.

In some embodiments, the anticancer agent is a cytotoxic drug, including those known by skill in the art and medical practitioners. Exemplary anticancer agents include topoisomerase I inhibitors, vinca alkaloids, alkylating agents (including platinum compounds), taxanes and others known to those of skill in the art.

In another embodiment, the composition of the present invention comprises from about 1 to about 100 μg drug/mg lipid. In another embodiment, the composition of the present invention comprises from about 1 to about 50 μg drug/mg lipid. In another embodiment, the composition of the present invention comprises from about 20 to about 50 μg drug/mg lipid. In another embodiment, the composition of the present invention comprises from about 10 to about 25 μg drug/mg lipid.

In another embodiment, the drug's concentration in the composition is 0.2 to 1.5 mg/ml. In another embodiment, the drug's concentration in the composition is 0.4 to 1.0 mg/ml. In another embodiment, the drug's concentration in the composition is 0.6 to 1.0 mg/ml. In another embodiment, the drug's concentration in the composition is 0.7 to 0.9 mg/ml.

In another embodiment, the amount of drug or labeled compound (encapsulated within the liposome or attached to the liposome) is from about 0.1 mg/ml to about 15 mg/ml. In another embodiment, the amount of drug or labeled compound is from about 0.5 mg/ml to about 15 mg/ml, about 0.5 mg/ml to about 10 mg/ml, about 0.1 mg/ml to about 10 mg/ml, about 0.5 mg/ml to about 5 mg/ml; about 0.5 mg/ml to about 3 mg/ml, about 0.5 mg/ml to about 2 mg/ml, about 0.5 mg/ml to about 1.5 mg/ml, about 0.8 mg/ml to about 3 mg/ml, about 0.8 mg/ml to about 2 mg/ml, about 0.8 mg/ml to about 1.5 mg/ml, about 0.7 mg/ml to about 3 mg/ml, about 0.7 mg/ml to about 2 mg/ml, about 0.7 mg/ml to about 1.7 mg/ml, about 0.7 mg/ml to about 1.5 mg/ml, about 0.7 mg/ml to about 1.4 mg/ml, about 0.7 mg/ml to about 1.3 mg/ml, about 0.5 mg/ml, about 0.7 mg/ml, about 0.8 mg/ml, about 0.9 mg/ml, about 1 mg/ml, about 1.1 mg/ml, about 1.2 mg/ml, about 1.3 mg/ml, about 1.4 mg/ml, about 1.5 mg/ml, about 1.6 mg/ml, about 2 mg/ml, about 3 mg/ml, about 4 mg/ml, about 5 mg/ml, about 6 mg/ml, about 7 mg/ml, about 8 mg/ml, about 9 mg/ml, about 10 mg/ml or about 15 mg/ml within the liposome.

In another embodiment, a composition as described herein comprises a single drug. In another embodiment, a composition as described herein comprises more than one drug. In another embodiment, a composition as described herein is a combination therapy.

In another embodiment, a composition as described herein comprises an alkaloid, an alkylating agent, an anti-tumor antibiotic, an antimetabolite, a hormone and hormone analog, immunomodulator, photosensitizing agent, antibody, peptide, anti-mitotic agent, or any combination thereof. In another embodiment, a composition as described herein comprises a plant alkaloid.

In another embodiment, the liposome of the present invention enables the delivery of a drug such as an anticancer agent without the induction of devastating side effects produced by the drug. This is often referred to as the therapeutic index, which describes the balance between the required dose to accomplish the destruction of the cancer cells compared to the dose at which the substance is unacceptably toxic to the individual. Thus the present invention bypasses the drawbacks-toxicity of most anticancer agents which often have a relatively small range of therapeutic index, (i.e., the narrow dosage range in which cancer cells are destroyed without unacceptable toxicity to the individual).

In another embodiment, the liposome of the present invention carries the substance as described herein, stabilizes it, penetrates through the BBB, and unloads the substance in a precise predetermined location or cell type (such as a cancer cell). In another embodiment, the liposome of the present invention carries the substance as described herein to cancerous cells. In another embodiment, the safety and specificity profile of the liposome of the present invention which carries an anti-cancer bring about the reduction of common side effects such as nausea and vomiting. In another embodiment, this long desired specificity allows the use of highly toxic compounds to be delivered to predetermined sites without unintended leakages of these toxic compounds. Thus the liposome carrier described herein, in some embodiments, reduces side effects common to a wide range of anticancer agents which include: hair loss (alopecia); appetite loss; weight loss; taste changes; stomatitis and esophagitis (inflammation and sores); constipation; diarrhea; fatigue; heart damage; nervous system changes; lung damage; reproductive tissue damage; liver damage; kidney and urinary system damage.

Marker

In another embodiment, a liposome composition of the invention comprises a labeled compound. In certain embodiments, the labeled compound comprises a radioisotopic moiety. In another embodiment, the substance to be carried by or via the circulatory system to the brain is a marker or a probe. In another embodiment, the substance to be carried by or via the circulatory system to the brain is a substance that can be precisely identified by radiological methods. In another embodiment, the substance is a labeled compound. In another embodiment, a marker or a probe is an agent useful in carrying out in vivo diagnostic procedures. In another embodiment, a "labeled compound" a "marker" or a "probe, are used interchangeably.

In another embodiment, the amount of labeled compound to be included in the compositions and formulations thereof, as described herein can be readily determined by the skilled artisan in view of the state of the art and teaching herein provided and depending on the labeled compound selected and the use intended for the composition or formulation, taking into account factors specific to both the labeled compound and the individual to be diagnosed.

In another embodiment, the labeled compound is an isotope. In another embodiment, the labeled compound is a radiolabeled compound. Exemplary labeled compounds include, for example, materials comprising radioisotopes (e.g., $^3$H, $^4$C, $^{67}$Ga, $^{111}$In, $^{125}$I, $^{131}$I, $^{133}$Xe, etc.), material comprising fluorescent moieties (e.g., fluorescein, fluorescein isothiocyanate, etc.), material comprising enzyme (e.g., peroxidase, alkaline phosohatase, etc.), as well as additional labeled compounds known to those of skill in the art. In another embodiment, the labeled compound is an imaging agent for all imaging modalities. In another embodiment, the labeled compound is a contrast agent. In another embodiment, the labeled compound comprises a radionuclide or a paramagnetic metal.

In another embodiment, the selection of the labeled compound and methods used in diagnosis will depend upon the brain tissue (e.g., malignant or non-malignant or tissue type to be investigated. In another embodiment, compositions of the invention incorporating $^{125}$I are particularly useful for identifying the presence and determining the severity (e.g., initially, during a course of treatment, after treatment) of cancer by gamma-counter.

Kits

In yet another embodiment of the invention, kits are provided which include liposomal compositions described herein. Certain embodiments of the liposome-containing compositions, include packaging and contained in a container.

In another embodiment, the kits, the liposome-containing compositions, as described herein is contained in a first container and one or more pharmaceutically acceptable carriers, excipients, diluents, stabilizers, or preservatives are contained in a second container. In another embodiment, provided kits incorporating the pharmaceutical formulations described herein, packaging and instructions for use.

Methods of Treatment

In a further embodiment, the present invention provides the use of the compositions (including targeted liposomes) and formulations thereof as described herein in the manufacture of a medicament. Particularly, the manufacture of a medicament for use in the treatment or diagnosis of conditions as described herein. In another embodiment, the pharmaceutical formulations are also intended for use in the manufacture of a medicament for use in treatment and diagnosis of the conditions and, in accordance with the methods, described herein.

In another embodiment, the invention provides methods for treating cancer (such as glioblastoma) comprising the step of a) administering a liposome as described herein to an individual in need thereof in an amount effective to treat cancer, wherein the drug is an anticancer agent. In another embodiment, the anticancer agent is an anti-glioblastoma agent. In another embodiment, cancer is brain cancer.

In another embodiment, the invention provides methods for treating a neurodegenerative disease (such as Alzheimer's disease) comprising the step of a) administering a liposome as described herein to an individual in need thereof in an amount effective to treat neurodegenerative disease, wherein the drug is a neurodegenerative disease therapeutic agent. Alzheimer's disease. In another embodiment, the drug is an Alzheimer's disease therapeutic agent. In another embodiment, the drug is a Parkinson disease therapeutic agent.

In another embodiment, the invention further provides methods of treatment comprising: step (a) is performed prior to, concurrently with or after combined modality therapy. In particular embodiments, the combined modality therapy, for cancer as an example, comprises chemotherapy, radiation therapy, or surgery. In some embodiments, the methods of treatment, step (a) is performed prior to, concurrently with or after adjunctive therapy.

In another embodiment, the adjunctive therapy comprises administration of one or more agents sensitizing the target cells or tissue to be further targeted by the liposomes as described herein. In another embodiment, the liposome composition as described herein is administered via parenteral administration. In another embodiment, parenteral administration is via injection or intravenous infusion.

In another embodiment, provided are methods of diagnosis comprising the steps of a) administering a liposome as described herein to an individual in need thereof in an amount effective for detection, wherein the targeted liposome comprises a labeled compound; and b) detecting the labeled compound. In another embodiment, the methods further comprise a step (c), comparing a level of labeled compound detected with a reference amount of the labeled compound detected at health or disease. In another embodiment, the reference amount is a threshold amount indicative of a disease.

In another embodiment, a composition comprising a liposome as described herein is utilized in photo-dynamic therapy. In another embodiment, a composition comprising a liposome as described herein is utilized as a drug carrier, an enhancer or both. In another embodiment, a composition comprising a liposome as described herein is utilized for controlled release of drugs including a photosensitizing agent in tumors.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Liposomes Having an Amyloid β (αβ) and/or Apolipoprotein E Recognition Peptide/s Penetrates from the Blood to the Brain without Hampering the Integrity of the BBB Materials Cholesterol (Ch), 1,2-dioleoyl-sn-glycero-3-phosphoethanolamine (DOPE), and 1,2-dioleoyl-sn-glycero-3-[phosphor-L-serine] (DOPS) or 1,2-dioleyi-ns-glycero-3-phosphocoline (DOPC) are purchased from Avanti Polar Lipids (Alabaster, Ala.). The fluorescence marker Texas Red was purchased from Molecular Probes (Eugene, Oreg.). Calcein purchased from Sigma (St. Louis, Mo.).

Liposome Preparation

Liposomes with a basic composition of Ch/DOPE/DOPS or Ch/DOPE/DOPC at a molar ratio of 1:1:1 were prepared in 10 mM phosphate buffered saline (PBS), pH 7.4. Phospholipids and Ch dissolved in chloroform mixed at the proper molar ratio. When needed, Texas Red and R18 added to this mixture at a concentration of 0.05-0.1 mol %. The conjugated short peptides (for example, 1,2-dioleoyl-sn-glycero-3-succinate-A-H-R-E-R-M-S-COOH, (SEQ ID NO: 6) and/or 1,2-dioleoyl-sn-glycero-3-succinate-A-L-R-K-L-R-K-R-L-L-R-COOH (SEQ ID NO: 3)) were added to the mixture at a concentration of 0.2-0.5 mol %. The synthesis, conjugation and purifying of the peptides: 1,2-dioleoyl-sn-glycero-3-succinate complex was conducted by peptide company (PiProteomics) according to our specific requirements.

The solvent was removed by rotary evaporation at 40° C. for 2 hrs. The dried lipid film was hydrated in PBS for 2 hrs, using an extended arm shaker. The multilamellar vesicles, formed by hydration and shaking, were reduced to a liposome diameter size range of 100-150 nm by gentle ultrasonic treatment using an ultrasonic cleaner (Model 75 HT, VWR) for 30 sec.

Liposomes were subjected to 5 freeze and thaw (F&S) cycles followed by extrusion through 100-nm-pore polycarbonate filters using an extrusion device (Northern Lipids Inc., Burnaby, BC, Canada). Liposomes were then lyophilized overnight using a Virtis Benchtop SLC lyophilizer (Model 4KBTXL-75) and kept under nitrogen in sealed bottles until use. As required, the size of the liposomes was further reduced using additional F&T cycles followed by extrusion through polycarbonate filters of 100 nm and 50 nm pore size.

1. Drug Loading (Hydrophilic and/or Lipophilic)

Water-soluble drugs such as Calcein dissolved in PBS at the highest concentration available were added to the dry liposomes at 5:1-30:1 ratio, gently mixed and incubated for 30 min at room temp. The mixture was brought to a volume of 1 ml and dialyzed against 500 ml PBS overnight. Drug concentrations were determined and the liposome injection dose was determined.

For lipid soluble drugs the liposome preparation process included two steps. Step I included mixing all the components (whose proportions vary according to the study) under magnetic stirring and heating from room temperature up to the "so-called" T2 temperature, which is above the phase-inversion temperature (PIT), to obtain a Water/Oil emulsion.

This was followed by a cooling process to the "so-called" T1 temperature, which is below the PIT, leading to the formation of an O/W emulsion. Several temperature cycles crossing the phase-inversion zone (PIZ) between T2 and T1 were then carried out. The temperature before dilution was determined at the beginning of the inversion process and is defined by a temperature range that is set at 1-3° C. from the beginning of the O/W emulsion.

Step II was an irreversible shock, induced by sudden dilution with cold water added to the mixture which has been maintained at the previously defined temperature. This was done in order to break the microemulsion system obtained in the PIZ, and lead to the formation of stable nanocapsules.

Afterwards, slow magnetic stirring was applied to the suspension for 5 min. Different composition proportions were prepared in order to explore the phase diagram. Three temperature cycles of heating and cooling at the rate of 4° C./min were applied between 85 and 60° C. The liposomes were loaded with the drug of choice and the concentration of the payload and the stability of the loaded liposomes in-vitro and in-vivo were tested. Each batch of conjugated peptides was subjected to a set of tests to evaluate the quality of the product before injection into animals.

Figure 3:
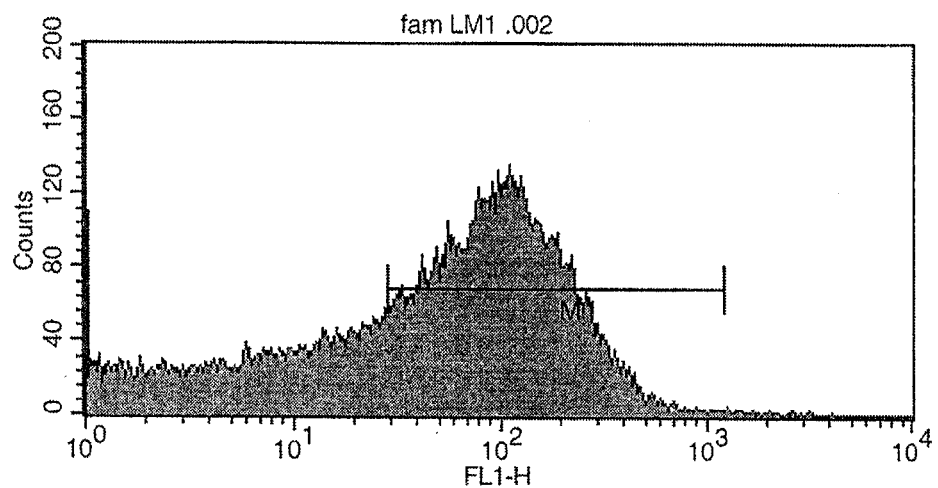
FIG. 3. Is a graph showing FACS recording of liposomes loaded with DNA labeled with FAM in the upper figure (A) and control empty liposomes at the lower figure (B). Free DNA was below the size that can be detected by the FACS
Figure 3:
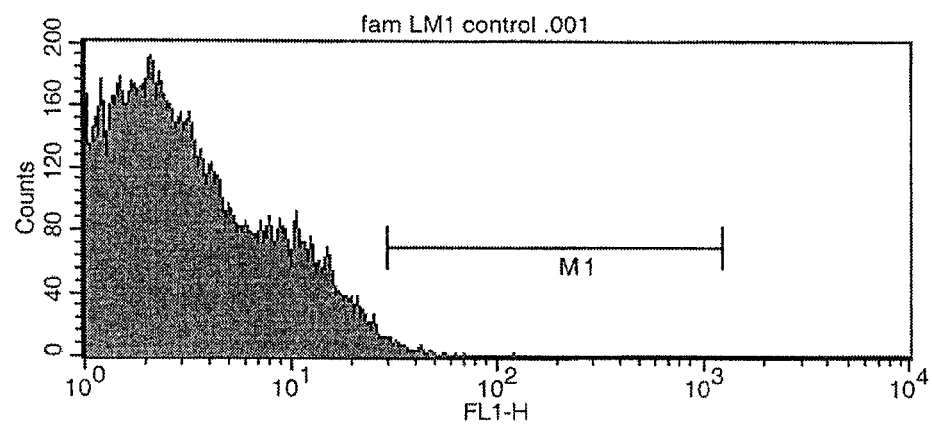

Further experiments engaged at loading nucleic acid molecules to the liposomes of the invention were carried out. Specifically, a DNA fragment (39 BPs labeled with fluorescent FAM) was loaded passively into the liposomes by adding 100 µg DNA dissolved in 0.2 ml of water to lyophilized liposomes followed by removal of the unencapsulated DNA by centrifugation in saline (1000 g, 5 min, 4° C.). The pellet was then washed by resuspension in saline, and the process was repeated four times. Loaded DNA was determined by running the liposomes in FACS measuring the distribution and content of DNA in the liposomes (FIG. 3). The data were compared to empty liposomes and to free labeled DNA. Since DNA is acting intracellularly it is important to use the pH sensitive liposomes e.g. containing 33% of phsphatidyl serine, to release the payload from the endosomes.

Then loading of onto the liposomes of the invention was carried out. Liposomes loaded passively could not hold the drugs inside the liposomes since during the dialysis the drug diffused back to the external solution. Therefore the procedure of remote loading (Zucker et al. 2009) was tested for Clorgyline. Loading was done by passive loading of the liposomes with 0.2 M of ammonium sulfate followed by the creation of a liposomal gradient by replacing the salt in the external liposome medium with iso-osmotic solution (with regard to plasma) of saline or sucrose. This was followed by three repeated dialysis cycles using 250 volumes of dialyzing medium for 1 volume of the liposome dispersion at 40° C. for 1 h, followed by a fourth dialysis step against 500 volumes of dialysis medium overnight. This resulted in trans-membrane ion gradients' magnitude of at least 1000 which actually create an anionic pump that sucked the mild cationic drug into the liposomes and securing these drugs within the liposomes by electric bonds.

Additionally, the final step of remote loading was achieved by incubation of Clorgyline with Ammonium sulfate preloaded liposomes for 10-480 min at 37° C., then cooling to 4° C. Non-entrapped drug was removed by centrifuging (1000 g, 5 min, 4° C.). The pellet was then washed by resuspension in saline, and the process was repeated four times. Following this procedure a concentration of 100 µg clorgyline/2.8 mg liposomes were measured from the extract of the liposomes.

Last, Dopamine was successfully loaded into the liposomes. Specifically, dissolving of Dopamine in water resulted in solution at pH-5.7 that was not compatible with the liposomes containing 33% phosphatidyl serine—pH sensitive liposomes designed to fuse at low pH. Since various drugs may present different pH when dissolved in water, the formulation of the liposomes was designed to carry drugs in a non-sensitive pH liposomes, e.g. the phosphatidyl serine was replaced with phosphatidyl choline as demostated by Allon at al. (2012). In short liposomes with a basic composition of Ch/DOPE/PC at a molar ratio of 1:1:1 were prepared in 10 mM phosphate buffered saline (PBS), pH 7.4. Phospholipids and Ch dissolved in chloroform were mixed at the proper molar ratio. The conjugated targeting peptide was added to the mixture at 0.5 mol %. The solvent was removed by rotary evaporation at 40° C. for 2 h followed by overnight lyophilization. The dried lipid film was hydrated in PBS for 2 hours, using an extended arm shaker. The multi-lamellar vesicles formed by hydration were reduced to 100 nm as follows: Liposomes were subjected to 5 freeze and thaw cycles, followed by extrusion through 200-nm—followed by 100 nm pore polycarbonate filters using an extrusion device (Northern Lipids Inc., Burnaby, BC, Canada). Liposomes were then lyophilized overnight using a Virtis Benchtop SLC lyophilizer (Model 4KBTXL-75) and kept under nitrogen in sealed vials until use. Utilizing the liposomes formulated with PC instead of PS enables using the remote loading drugs with wide range of pH and stabilized the system. Loading of DNA, siRNA or plasmids require the PS liposomes for endosomal escape e.g release of the payload to the cytoplasm and can be done by passive loading.

2. Evaluation of the Ability of the Targeted Liposomes to Cross the BBB and Release their Payload in the Brain Two main SJL/female mice groups were tested:
1. Control—Calcein loaded non targeted liposomes treated group
2A. Calcein loaded liposomes conjugated H-R-E-R-M-S-COOH (APP327-332, SEQ ID NO: 5) a binding site of Amyloid beta. The peptide is covalently conjugated to 1,2-dioleoyl-sn-glycero-3-succinate through amino acid spacer.
2B. Calcein loaded liposomes Ch/DOPE/DOPS conjugated to L-R-K-L-R-K-R-L-L-R (hApoE141-150, SEQ ID NO: 2). The peptide was covalently conjugated to 1,2-dioleoyl-sn-glycero-3-succinate through amino acid spacer.

Targeting peptides were inserted into the phospholipids mixture during the preparation of the liposomes at 0.5 mol % of the original mixture in the presence of 0.25 mol % Texas Red.

Every group included 4 mice. The mice were injected (tail vain), equal amount of calcein per kg mice. Three hours later mice were anesthetized, perfused with saline and fixed with paraformaldehide in the presence of 30% sucrose for a week and then serially sliced to 40 μm thick frozen sections. Observations were performed using specific lasers for activation of Texas Red and/or Calcein.

Evaluations of the efficacy of the treatments were based on laser confocal microscope of brain slices 40 μm thick.

In conclusion, as full length or long segments of Aβ or ApoE may have damaging side effects, a short segment of this peptides that is recognized by the BBB transporter but has no further undesired functional effects was used. Both liposome-peptide preparations (2A and 2B), targeting two distinct BBB domains, had minimal in-vivo biological effects. Thus these peptides can be used as targeting conjugates to liposomes for BBB attachment and crossing and thus enable the long desired promotion of transport of compounds into the brain via the circulatory system. Moreover, these short peptides proved to have negligible immunogenicity compared to the longer, source, peptides.

To evaluate the efficacy of these peptides in liposomal transport from the blood to the brain via the BBB, liposomes labeled with Texas Red were prepared (red fluorescent dye) and loaded with Calcein (yellowish-green fluorescent dye). Liposomes were conjugated with the peptide of SEQ ID NO: 1 or the peptide of SEQ ID NO: 2 on their surface as described in FIGS. 1 and 2. Control liposomes were without any such transporter peptide. The liposomes were injected into the tail-vain of awaked mice. Three hours later mice were anesthetized, perfused with saline, and the brains were removed for histological evaluation. Evaluation of the fluorescence emission of each dye was measured utilizing a confocal microscope.

Figure 2:
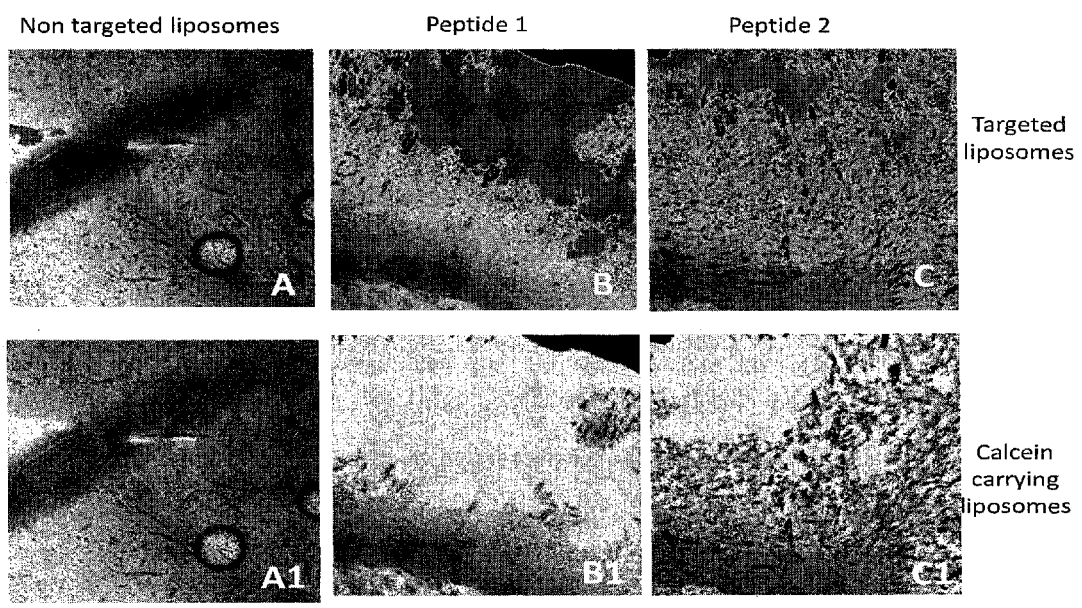
FIG. 2. Is a micrograph of brain slices evaluating the transport and release of liposomes and their payload in the brain of mice following intravenous injection. A—mice injected with non-targeted liposomes. B and C—mice injected with liposomes conjugated to the transporter peptides of SEQ ID NOs: 1 and 2, respectively. A1, B1, and C1 depicted the release of the Calcein payload from the liposomes. Only liposomes with the peptide targeting the BBB (B, B1, C, C1) accumulate in the brain (light grey). The negative controls do not show such an accumulation (A, A1).

The mice injected with liposomes conjugated with the transporter peptide, displayed abundant labeling of liposomes as well as their payload accumulated in their target organ, the brain (FIG. 2). In contrast, the non-targeting control liposomes only showed minimal labeling in a few capillaries (FIG. 2).

Thus, as designed, the present invention enables the delivery of compounds to the brain thus enabling the treatment of brain pathologies such as glioblastoma, or neurodegenerative diseases.

The invention claimed is:

1. A composition comprising a liposome and a liposome-anchored blood-brain-barrier (BBB) recognition peptide covalently conjugated to said liposome, said covalently conjugated is conjugated via a peptide bond between a carboxyl end of a succinate group within said liposome lipid bilayer and an amino group of said peptide, wherein said BBB recognition peptide comprises the amino acid sequence AHRERMS (SEQ ID NO: 6) or ARERMS (SEQ ID NO: 4).

2. The composition of claim 1, wherein said liposome further comprises a second peptide comprising the amino acid sequence of SEQ ID NO: 2.

3. The composition of claim 2, wherein said second peptide consists the amino acid sequence of ALRKLRKRLLR (SEQ ID NO: 3).

4. The composition of claim 1, wherein said conjugated is conjugated via a peptide bond between a carboxyl end of a succinate group within the liposomal lipid bilayer and the amino group of said at least one spacer amino acid.

5. The composition of claim 1, wherein said peptide consists the amino acid sequence AHRERMS (SEQ ID NO: 6).

6. The composition of claim 1, wherein said liposome further comprises a brain therapeutic compound.

7. The composition of claim 1, wherein said liposome further comprises a brain probing agent.

8. The composition of claim 1, wherein said liposome comprises cholesterol (Ch), 1,2-dioleoyl-sft-glycero-3-phosphocholine (DOPC), 1,2-dioleoyl-snglycero-3-phosphoethanolamine (DOPE).

9. The composition of claim 8, wherein the weight ratio of: Ch, DOPC, and DOPE is 1:1:1.

10. The composition of claim 1, wherein said liposome comprises cholesterol (Ch), 1,2-5 dioleoyl-sft-glycero-3-[phosphor-L-serine] (DOPS), 1,2-dioleoyl-sn-glycero-3-phosphoethanolamine (DOPE).

11. The composition of claim 10, wherein the weight ratio of: Ch, DOPS, and DOPE is 10 1:1:1.

12. The composition of claim 1, wherein said composition is lyophilized.

13. The composition of claim 1, wherein the liposome's diameter is between 10 nm to 200 nm.

14. A method for delivering a liposome into a subject's brain, comprising administering to said subject the composition of claim 1, thereby delivering a liposome into a subject's brain.

15. The method of claim 14, wherein said delivering comprises systemically administering.

16. A process for the preparation of a liposome conjugated to a peptide comprising at least one spacer amino acid followed by an amino acid sequence selected from the group consisting of SEQ ID NOs: 3, 4, or 6, comprising the steps:
(a) dissolving in ethanol or chloroform: (1) Cholesterol (Ch), 1,2-dioleoyl-5nglycero-3-phosphocholine (DOPC), and 1,2-dioleoyl-sn-glycero-3-phosphoethanolamine (DOPE); or (2) Cholesterol (Ch), 1,2-dioleoyl-5n-glycero-3-[phosphor-L-serine] (DOPS), and 1,2-dioleoyl-sn-glycero-3-phosphoethanolamine (DOPE);

(b) adding to the mixture of step (a) a peptide comprising at least one spacer amino acid followed by an amino acid sequence selected from the group consisting of SEQ ID NOs: 3, 4, or 6 conjugated to either 1,2-dioleoyl-5n-glycero-3-succinate or 1,2-dioleoyl-5n-glycero-3-succinate at a concentration of 0.1-1 mol %;

(c) removing said chloroform and obtaining a dried lipid film; and (d) hydrating said dried lipid film in an isotonic buffer; thereby obtaining a liposome conjugated to a peptide comprising at least one spacer amino acid followed by an amino acid sequence selected from the group consisting of SEQ ID NOs: 3, 4, or 6.

17. The process of claim 16, wherein the weight ratio of: Ch, DOPC, and DOPE or the weight ratio of: Ch, DOPS, and DOPE is 1:1:1.

18. The process of claim 16, wherein the liposome's diameter is between 10 nm to 200 nm.

19. The process of claim 16, further comprising extruding the liposome through a 50 nm to 100 nm pore filter.

20. The process of claim 16, further comprising lyophilizing said liposome.

21. The process of claim 16, further comprising loading a hydrophilic drug onto said 5 liposome in an isotonic buffer in an amount equal to w/w ratio in the range from 2:1 to 100:1 drug to dry liposome.

22. The process of claim 16, further comprising loading a lipid soluble drug onto said liposome comprising:

(a) heating a loading composition comprising said lipid soluble drug and said 10 liposome to a temperature that is 0.01° C. to 5° C. above the phase-inversion temperature thus obtaining a water in oil emulsion;

(b) cooling said loading composition to a temperature that is 0.01° C. to 10° C. below the phase-inversion temperature thus obtaining an oil in water emulsion.

23. The process of claim 22, wherein steps (a) and (b) form a cycle that is repeated at least 15 twice.

24. The process of claim 22, wherein said heating and said cooling are performed at a rate of 1° C. to 10° C./min.

25. The process of claim 22, wherein said heating is heating to a temperature between 75° C. to 95° C.

26. The process of claim 22, wherein said cooling is cooling to a temperature between 50° C. to 70° C.

27. A liposome obtained by the process of claim 16.

* * * * *

SEQUENCE LISTING

<160> NUMBER OF SEQ ID NOS: 6

<210> SEQ ID NO 1
<211> LENGTH: 5
<212> TYPE: PRT
<213> ORGANISM: homo sapiens

<400> SEQUENCE: 1

Arg Glu Arg Met Ser
1               5

<210> SEQ ID NO 2
<211> LENGTH: 10
<212> TYPE: PRT
<213> ORGANISM: homo sapiens

<400> SEQUENCE: 2

Leu Arg Lys Leu Arg Lys Arg Leu Leu Arg
1               5                   10

```
<210> SEQ ID NO 3
<211> LENGTH: 11
<212> TYPE: PRT
<213> ORGANISM: homo sapiens

<400> SEQUENCE: 3

Ala Leu Arg Lys Leu Arg Lys Arg Leu Leu Arg
1               5                   10

<210> SEQ ID NO 4
<211> LENGTH: 6
<212> TYPE: PRT
<213> ORGANISM: homo sapiens

<400> SEQUENCE: 4

Ala Arg Glu Arg Met Ser
1               5

<210> SEQ ID NO 5
<211> LENGTH: 6
<212> TYPE: PRT
<213> ORGANISM: homo sapiens

<400> SEQUENCE: 5

His Arg Glu Arg Met Ser
1               5

<210> SEQ ID NO 6
<211> LENGTH: 7
<212> TYPE: PRT
<213> ORGANISM: homo sapiens

<400> SEQUENCE: 6

Ala His Arg Glu Arg Met Ser
1               5
```